United States Patent [19]

Taniguchi et al.

[11] Patent Number: 4,925,934
[45] Date of Patent: May 15, 1990

[54] PROCESS FOR PREPARATION OF BETA-LACTAM DERIVATIVES

[75] Inventors: Masatoshi Taniguchi; Michio Sasaoka; Kiyotoshi Matsumura; Ichiro Kawahara; Kenji Kaze; Daisuke Suzuki; Akihiro Shimabayashi, all of Tokushima, all of Japan

[73] Assignees: Otsuka Kagaku Kabushiki Kaisha, Osaka; Taiho Pharmaceutical Co., Ltd., Tokyo, both of Japan

[21] Appl. No.: 317,322

[22] Filed: Mar. 1, 1989

[30] Foreign Application Priority Data

Mar. 2, 1988 [JP] Japan .................................. 63-50230

[51] Int. Cl.$^5$ .................. C07D 499/08; A61K 31/425
[52] U.S. Cl. ..................................... 540/310; 540/350
[58] Field of Search ................ 514/195, 192; 540/310, 540/350

[56] References Cited

PUBLICATIONS

Kametani, T. et al., "The Deblocking of Cepalosporin Benzhydryl Esters with Formic Acid", *Chemical Pharmaceutical Bulletin*, vol. 30, No. 12 (1982), pp. 4545–4547.
Tsuji, T. et al., "Synthetic Studies on β–Lactam Antibiotics VII", *Tetrahedron Letters*, No. 30, pp. 2793–2796.
*Journal of The American Chemical Society*, No. 91, Sep. 24, 1969, pp. 5674–5675.

*Primary Examiner*—Nicholas S. Rizzo
*Attorney, Agent, or Firm*—Armstrong, Nikaido, Marmelstein, Kubovcik & Murray

[57] ABSTRACT

The invention provides a process for preparing a β-lactam derivative represented by the formula

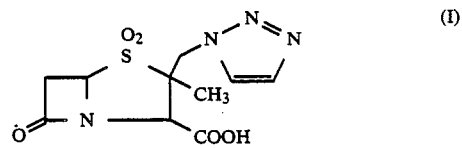

the process comprising reacting a β-lactam derivative represented by the following formula (II) and having a protected carboxyl group with a cresol;

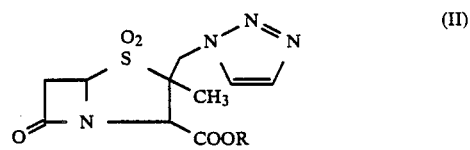

wherein R represents a benzyl group having an electron-donating group as a substituent on the phenyl ring, a diphenylmethyl group which may have an electron-donating group as a substituent on the phenyl ring or a tert-butyl group.

6 Claims, No Drawings

PROCESS FOR PREPARATION OF BETA-LACTAM DERIVATIVES

The present invention relates to a process for preparing a β-lactam derivative.

A β-lactam derivative represented by the formula

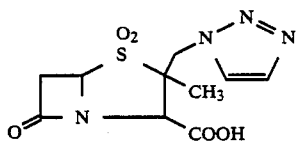

(I)

has been found to be useful as a β-lactamase inhibitor. However, this finding was made only recently. Thus processes are little known for preparing the β-lactam derivative of the formula (I) by removing a carboxyl-protecting group from a β-lactam derivative having protected carboxyl group and represented by the formula

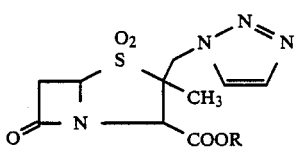

(II)

wherein R represents a benzyl group having an electron-donating group as a substituent on the phenyl ring, a diphenylmethyl group which may have an electron-donating group as a substituent on the phenyl ring or a tert-butyl group.

Heretofore elimination of carboxyl-protecting group has been accomplished by, for example, subjecting the β-lactam derivative of the formula (II) to catalytic reduction using a noble metal catalyst or to treatment with an acid. The acid treatment methods include methods using trifluoroacetic acid (Journal of The American Chemical Society, 91, 5674, 1969), methods using formic acid (Chemical Pharmaceutical Bulletin, 30, 4545, 1982), methods involving a reaction of the derivative with aluminum chloride in the presence of anisole (Tetrahedron Letters, 2793, 1979), etc. However, these conventional methods have the following drawbacks.

The catalytic reduction method using a noble metal catalyst requires a large amount of expensive noble metal catalyst, and poses the problems of being unable to remove the protective group if it is tert-butyl, and being unlikely to remove the protective group if it is a benzyl group having an electron-donating group as a substituent on the phenyl ring or a diphenylmethyl group having an electron-donating group as a substituent on the phenyl ring.

While the β-lactam derivative of the formula (I) is unstable under the influence of strong acid, methods using acids necessitate at least a stoichiometric amount of strong acid and therefore have the disadvantage of decomposing the produced β-lactam derivative of the formula (I) due to the action of acid, decreasing the yield of the compound of the formula (I).

Stated more specifically, if the reaction is conducted using a large amount of, e.g., trifluoroacetic acid to remove the protective group from the β-lactam derivative of the formula (II), the reaction raises the problems: after completion of reaction, the recovery of acid for re-use is likely to cause the loss of acid in great amount and decomposes the produced compound of the formula (I) which is unstable to trifluoroacetic acid, thereby further reducing the yield of the compound of the formula (I) (see Comparison Example 1 to follow).

The method using formic acid encounters the same problems, and requires an excess amount of expensive 98-100% formic acid as a solvent. If the volatiles are distilled off under reduced pressure to recover the formic acid for re-use, the compound of the formula (I), being unstable to an acid, is made to decompose to decrease the yield of produced compound of the formula (I) (see Comparison Example 2 to follow).

Further the methods wherein the compound of the formula (II) is reacted with aluminum chloride in the presence of anisole have the drawbacks of: essentially using aluminum chloride which brings about exothermic reaction with water in air, thereby producing hydrochloric acid which is difficult to handle; causing the compound of the formula (I) to decompose in the reaction mixture which was made strongly acidic during reaction or aftertreatment, thereby lowering the yield thereof; and requiring disposal of great amount of aluminum chloride after completion of reaction (see Comparison Example 3 to follow).

An object of the present invention is to provide a process, free of the foregoing prior art problems, for preparing the β-lactam derivative of the formula (I) in high yields by performing a safe and simplified procedure in a commercially advantageous manner.

We conducted extensive research to develop a problem-free process for preparing the β-lactam derivative of the formula (I) in high yields, and found that the desired compound can be prepared in high yields by using cresol among phenols, more specifically reacting the cresol with the compound of the formula (II) at a temperature of about 50° to about 55° C. without addition of acid. The present invention has been accomplished on the basis of this novel finding.

According to the present invention, there is provided a process for preparing the β-lactam derivative of the formula (I), the process comprising reacting the β-lactam derivative of the formula (II) having a protected carboxyl group with a cresol.

Examples of the carboxyl-protecting group represented by R in the formula (II) are p-methoxybenzyl, 3,4,5-trimethoxybenzyl, 2,4-dimethoxybenzyl, 3,5-dimethoxy-4-hydroxybenzyl, 2,4,6-trimethylbenzyl, diphenylmethyl, ditolylmethyl, dianisylmethyl, tert-butyl, etc.

Examples of cresols useful in the present invention are o-cresol, m-cresol, p-cresol, etc. among which m-cresol is preferred.

In practicing the present invention, the compound of the formula (II) is reacted with cresol. Optimum reaction temperature is about 50° to about 55° C. The cresol is used in an amount of about 5 to about 15 times the weight of the compound of the formula (II). According to the invention, an acid catalyst need not be added, eliminating the undesired possibility of the acid lowering the yield of desired compound.

After completion of reaction, the compound of the formula (I) can be isolated from the reaction product by usual aftertreatment. For example, sodium carbonate or hydrogencarbonate and hydrophobic organic solvent are added to the reaction product to form an aqueous layer containing the compound of the formula (I), and making the aqueous layer acidic, thereby precipitating the desired compound of the formula (I). The solvent and cresol used can be recovered for re-use by distilling the organic layer.

A pharmaceutically acceptable salt of the compound of the formula (I) can be easily produced from the compound of the formula (I) by conventional methods.

According to the present invention, the carboxyl-protecting group can be removed in a simple manner from the compound of the formula (II) having protected carboxyl group. The process of the present invention eliminates the need for large amount of acid which is required in conventional processes, so that the compound of the formula (I) produced in the reaction can be obtained in high yields. Further, the present invention enables efficient recovery of cresol, solvent and the like used, hence also economically advantageous.

The present invention will be described below in greater detail with reference to the following Examples and Comparison Examples wherein the words "compound (I)" and "compound (II)" are short for "compound of the formula (I)" and "compound of the formula (II)", respectively.

EXAMPLE 1

A 10 g quantity of compound (II) wherein R is a diphenylmethyl group was reacted for 2 hours with 80 ml of m-cresol heated to 50° to 55° C. while the reaction system was maintained at the same temperature. After completion of reaction, 240 ml of methyl isobutyl ketone was added and the mixture was cooled to 0° to 5° C. To the mixture were added 23 ml of water and 2.3 g of sodium hydrogencarbonate after which the mixture was extracted. After the organic layer was separated, 12 ml of water and 0.7 g of sodium hydrogencarbonate were added and the mixture was extracted. The aqueous layers were mixed, washed with 18 ml of methyl isobutyl ketone, cooled to 0° to 5° C. and adjusted with 6N hydrochloric acid to a pH of 1. The precipitated compound (I) was filtered for separation. The filter cake was washed with a small amount of cold water and dried, giving white crystals of compound (I) in a yield of 95%.

The obtained compound was identical in NMR spectrum with the compound (I) otherwise synthesized.

EXAMPLE 2

The same procedure as in Example 1 was repeated with the exception of using a compound (II) wherein R is a p-methoxybenzyl group, giving a compound (I) in a yield of 96%.

EXAMPLE 3

The same procedure as in Example 1 was repeated with the exception of using a compound (II) wherein R is a tert-butyl group, giving a compound (I) in a yield of 91%.

COMPARISON EXAMPLE 1

A 0.5 g quantity of compound (II) wherein R is a diphenylmethyl group was suspended in 5 ml of 1,2-dichloroethane, and 0.11 ml of anisole was added to the suspension. Thereafter 0.54 ml of trifluoroacetic acid was added dropwise to the mixture to give a solution. The solution was reacted while being maintained at 0° C. until the maximum yield of compound (I) was attained.

The same reaction as above was repeated except for a reaction temperature of 20° C.

Table 1 below shows the results of HPLC analysis.

TABLE 1

| Temperature | Time until attainment of maximum yield | Yield (%) | Percent unreacted compound (%) |
| --- | --- | --- | --- |
| 0° C. | 1 hr | 56.5 | 26.6 |
|  | 2 hr | 34.3 | 13.9 |
| 20° C. | 30 min | 46.1 | 10.0 |
|  | 2 hr | 23.4 | 7.2 |

Table 1 shows the decomposition of desired compound taking place prior to consumption of starting compound.

COMPARISON EXAMPLE 2

A 0.5 g quantity of compound (II) wherein R is a diphenylmethyl group was reacted for 30 minutes with 2.5 ml of 99% formic acid heated to 40° C. while the reaction system was maintained at the same temperature. HPLC analysis shows the following results.

The starting compound was consumed to about 3% in 30 minutes.

A large amount of by-products were produced.

The desired compound (the compound (I)) was produced in a yield of 20%.

A 0.5 g quantity of compound (II) wherein R is a diphenylmethyl group was added to 1 ml of 99% formic acid heated to 30° C., and 0.22 ml of anisole was added dropwise. The mixture was stirred for 3 hours while being maintained at the same temperature. HPLC analysis reveals the following results.

10.5% of the starting compound remained unreacted.

The desired compound (compound (I)) was produced in a yield of 46.7%.

The extension of reaction time decreased the yield of compound (I) due to the decomposition.

COMPARISON EXAMPLE 3

A 408 mg quantity of aluminum chloride was dissolved in 10 ml of nitromethane. The solution was added to a solution of 0.5 g of compound (II) wherein R is a diphenylmethyl group and 0.66 ml of anisole in 10 ml of dichloromethane while being cooled in an ice bath. The mixture was reacted for 1 hour with cooling.

The reaction was extended for further 1 hour and then the yield was reduced.

Table 2 below shows the results of HPLC analysis.

TABLE 2

| Time | Percent unreacted compound (%) | Yield (%) |
| --- | --- | --- |
| 1 | 3.7 | 27.1 |
| 2 | 0.4 | 23.7 |

For further comparison, the same procedure as above was repeated with the exception of conducting reactions under the conditions shown below in Table 3.

Table 3 also shows the results.

TABLE 3

| Compound (II) (g) | AlCl$_3$ (eq.) | Anisole (eq.) | Time until attainment of maximum yield | Yield (%) |
| --- | --- | --- | --- | --- |
| 0.5 | 3 | 1 | 1 | 27.4 |
| 0.5 | 2 | 6 | 5 | 26.9 |

TABLE 3-continued

| Compound (II) (g) | AlCl₃ (eq.) | Anisole (eq.) | Time until attainment of maximum yield | Yield (%) |
| --- | --- | --- | --- | --- |
| 0.5 | 1.2 | 6 | 5 | 11.0 |

We claim:

1. A process for preparing a β-lactam derivative represented by the formula

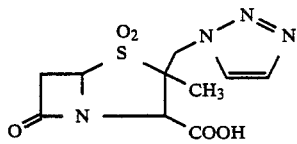

(I)

the process consisting essentially of reacting a β-lactam derivative represented by the following formula (II) and having a protected carboxyl group with a cresol;

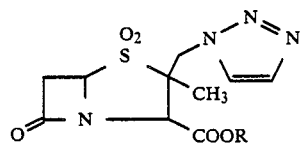

(II)

wherein R represents a benzyl group having an electron-donating group as a substituent on the phenyl ring, a diphenylmethyl group which may have an electron-donating group as a substituent on the phenyl ring or a tert-butyl group.

2. A process according to claim 1 wherein R in the formula (II) is at least one member selected from the group consisting of p-methoxybenzyl, 3,4,5-trimethoxybenzyl, 2,4-dimethoxybenzyl, 3,5-dimethoxy-4-hydroxybenzyl, 2,4,6-trimethylbenzyl, diphenylmethyl, ditolylmethyl, dianisylmethyl and tert-butyl.

3. A process according to claim 1 wherein the cresol is at least one member selected from the group consisting of o-cresol, m-cresol and p-cresol.

4. A process according to claim 1 wherein the cresol is m-cresol.

5. A process according to claim 1 wherein the cresol is used in an amount of 5 to 15 times the weight of β-lactam derivative of the formula (II).

6. A process according to claim 1 wherein the reaction is carried out at 50° to 55° C.

* * * * *